United States Patent [19]

Kelso et al.

[11] Patent Number: 4,611,603
[45] Date of Patent: Sep. 16, 1986

[54] CALIBRATED EXAMINING GLOVE

[76] Inventors: Jimmie J. Kelso, 11812 W. 149th St., Olathe, Kans. 66062; Russell M. Hustead, 10809 Horton, Overland Park, Kans. 66211

[21] Appl. No.: 706,761

[22] Filed: Feb. 28, 1985

[51] Int. Cl.$^4$ .............................................. A61B 5/10
[52] U.S. Cl. .................................................. 128/775
[58] Field of Search .................. 128/361, 775, 778; 2/160

[56] References Cited

U.S. PATENT DOCUMENTS

| 2,241,451 | 5/1941 | Fist | 128/778 |
| 2,394,140 | 2/1946 | Biscow | 128/361 |
| 2,847,676 | 8/1958 | Scott | 2/159 |
| 2,924,220 | 2/1960 | VonMicsky | 128/775 |
| 3,097,637 | 7/1963 | Horton | 128/775 |
| 3,126,890 | 3/1964 | Deming, Sr. | 128/361 |
| 3,643,651 | 2/1972 | Cuadros | 128/775 |
| 4,016,867 | 4/1977 | King et al. | 128/778 |
| 4,141,345 | 2/1979 | Allen et al. | 128/775 |
| 4,207,902 | 6/1980 | Krementsov | 128/775 |
| 4,245,656 | 1/1981 | Farr et al. | 128/775 |

FOREIGN PATENT DOCUMENTS 11910 of 1897 United Kingdom ............... 128/361

Primary Examiner—William E. Kamm
Attorney, Agent, or Firm—Litman, Day and McMahon

[57] ABSTRACT

An examining glove is provided which includes a front, a back, a first finger and a second finger. A measuring string has a distal end attached to the first finger and is slidably connected to the second finger by a flexible tube extending from the second finger to the glove front or back and slidably receiving the measuring string. A scale is associated with the tube on the glove front or back and is adapted for determining measuring string slippage. The measuring string terminates in a proximate end which dangles freely from the tube.

20 Claims, 4 Drawing Figures

CALIBRATED EXAMINING GLOVE

BACKGROUND OF THE INVENTION

1. Field of the Invention

The present invention relates generally to medical examining instruments and in particular to a calibrated glove for taking obstetrical measurements.

2. Description of the Prior Art

In medical practice, and particularly obstetrics, internal measurements are often necessary for purposes of evaluating the patient's condition. In obstetrics, certain internal measurements are important prior to the onset of labor to anticipate potential delivery problems and other measurements are important during labor to monitor the patient's and her baby's progress.

Specifically, the conjugate diameter of the pelvic inlet, as measured from the promontory of the sacrum to the symphysis pubis is important to determine if the pelvic inlet is of sufficient size to permit normal delivery. In practice, a measurement comprising the diagonal conjugate is generally taken from the sacral promontory to the lower margin of the symphysis pubis. The true obstetric conjugate can then be determined by subtracting 1.5 to 2 centimeters from the diagonal conjugate. "Williams Obstetrics," by Jack A. Pritchard, Paul C. MacDonald and Norman F. Gant, 17th Ed. (1985), published by Appleton-Century-Krafts, Inc., New York, N.Y.

In a common prior art method of measuring the conjugate diameter, the examiner inserts his or her index and middle fingers into the patient's vagina and engages the sacral promontory with the tip of the middle finger. The index finger of the other hand is then placed against the symphysis pubis and the base of the inserted index finger and the inserted hand is withdrawn so that the noted distance can be measured. The Biscow U.S. Pat. No. 2,394,140 discloses a glove with scales along the index finger for measuring the conjugate diameter. Also, the Cuadros U.S. Pat. No. 3,643,651 discloses a scale with a stirrup for placing over the examiner's middle finger and a calibrated strip extending therefrom.

Another important pre-labor obstetric measurement is the bisischial diameter, which is defined as the distance between the ischial spines at midpelvis. The fetal head must be small enough to pass between the ischial spines. Prior art devices for determining the bisischial diameter include that shown in the Horton U.S. Pat. No. 3,097,637 which includes an elongated stem with a short length of chain attached to one end and terminating in a ring. The ring is placed over a finger of the examiner and engaged against one of the ischial spines with the end of the stem engaging the other ischial spine. If the chain can be fully extended the bisischial diameter is considered adequate for delivery of a normal-sized fetus.

The aforementioned obstetric measurements are significant for determining if a disproportion exists between the size of the baby's head and the mother's pelvis prior to the onset of labor. By prediagnosing such a condition, the physician can determine if a delivery by cesarean section is indicated on the basis of pelvic contracture.

Another important obstetrical internal dimension is the diameter of the patient's cervix. Prior to the onset of labor a normal cervical canal has a diameter of zero to three centimeters. During labor, dilatation to approximately ten centimeters, a condition often referred to as "complete" or "fully dilated", must occur to pass the head of the average fetus through the cervix. Accordingly, the patient's progress through the first stage of labor can be determined by monitoring the cervical diameter. The patient's rate of change of cervical dilatation is significant to the physician, and can be determined from accurate and periodic measurements of the cervical diameter taken between the lower lips or rims of the cervix at the level of the internal os. The cervical diameter may also be important in detecting the premature onset of labor and in monitoring the effectiveness of tocolytic drugs in slowing or halting dilatation and the progress of labor.

A common method of roughly approximating the patient's cervical diameter involves the insertion of two or more fingers into the vagina and thence digitally contacting the lips or rims of the cervix. Based upon the relative position of his or her fingers, the examiner estimates the patient's cervical dilatation. However, digitally estimating the cervical diameter in this subjective manner tends to yield relatively inaccurate results which can vary widely between different examiners. For example, the size of the examiner's fingers and his or her experience might influence the estimation of the patient's dilatation. There is also a human tendency to overstate the true amount of dilatation to reassure the laboring patient that delivery will come soon and that her suffering will end. Furthermore, during labor a patient may be checked by several different examiners, whose methods and results may not be consistent.

The lack of accurate information on the cervical dilatation of patients is, at best, a source of frustration to obstetricians who, because of very tight schedules, are often not summoned until the woman is thought to be complete. Obviously if the patient is misdiagnosed as being complete, the obstetrician may arrive well before his or her presence is required. On the other hand, understating the patient's dilatation can have the opposite effect. Most importantly, accurate detection of a patient's lack of progress in labor at an early stage serves to alert the physician that further evaluation and alternative therapy may be indicated.

Various devices are known for measuring cervical dilatation. For example, the Von Micsky U.S. Pat. No. 2,924,220 and the Krementsov U.S. Pat. No. 4,207,902 U.S. patents show devices with arms for engaging the lips of the cervix and providing a measurement reading. However, such devices tend to be impractical, cumbersome, painful and relatively expensive. Furthermore, they require sterilization between each insertion to avoid the introduction of bacteria into the vagina and uterus.

The Farr et al. U.S. Pat. No. 4,245,656 discloses obstetric gloves with a measuring string coiled within one finger and extending to an adjacent finger. However, the measuring string of this device cannot be reset with the examiner's fingers inserted in the patient. Also, the fingers must be withdrawn to determine the measurement.

Another disadvantage with cervical measurements taken digitally relates to the possibility of introducing bacteria into the patient. Although standard procedure is for the examiner to wear a sterilized glove, cervical measurements taken digitally may be repeated often during labor, in part because of the relative uncertainties in the measurements. The frequency of examination not only increases the risk of infection but also adds to the discomfort of the patient.

Fetal progress during labor is monitored by comparing the position of the fetal head with respect to the ischial spines of the mother. The fetal position is designated by stations indicating the distance in centimeters between the lowermost portion of the fetal head and the bisischial diameter. Negative stations indicate the fetal head being located above the bisischial diameter and positive stations indicate a position below. When the fetal head reaches station plus five it is usually visible and is said to be "crowning". As with other obstetric measurements, the baby's descent station is often estimated subjectively by digital examination with resulting inaccuracies.

Heretofore there has not been available an examining glove for taking the aforementioned measurements with the advantages and features of the present invention.

SUMMARY OF THE INVENTION

In the practice of the present invention, an examining glove is provided which includes a front, a back, a cuff and first and second fingers each having a tip and a base. A measuring string has a distal end attached to the first finger between its tip and base. The measuring string is connected to the second finger by a flexible guide tube which slidably receives the measuring string. The guide tube terminates at a distal end between the second finger tip and base and at a proximate end in proximity to the glove cuff. The guide tube extends along the second finger and the glove front. A scale is associated with the guide tube and is adapted for determining slippage of the measuring string. The measuring string terminates in a proximate end which dangles freely from the guide tube proximate end.

OBJECTS OF THE INVENTION

The principle objects of the present invention are: to provide a calibrated examining glove; to provide such a glove which is adapted for taking internal body measurements; to provide such a glove which is particularly adapted for obstetrical use; to provide such a glove which is adapted for measuring the conjugate diameter of a patient; to provide such a glove which is adapted for measuring the bisischial diameter of a patient; to provide such a glove which is adapted for measuring the cervical dilatation of a pregnant patient; to provide such a glove which is adapted for measuring fetal advancement during labor; to provide such a glove which provides accurate measurements; to provide such a glove which provides measurements which do not vary appreciably between different examiners; to provide such a glove which is adapted to accurately monitor changes in the aforementioned internal body dimensions; to provide such a glove which is adapted to monitor the rate of change of the aforementioned internal body dimensions; to provide such a glove which may be used to reduce the number of examinations required during pregnancy and labor by providing more accurate measurements than were heretofore achieved using manual examination techniques; to provide such a glove which tends to reduce the risk of infection during pregnancy and labor because its required frequency of use is lower than with prior art gloves and devices; to provide such a glove with a measuring device which may be reset from outside the patient with the glove in place; to provide such a glove wherein the patient's internal dimensions can be observed on the outside; to provide such a glove which may be produced economically enough to be disposable after each use; to provide such a glove which can be resterilized; and to provide such a glove which is efficient in operation and particularly well adapted for the proposed usages thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

Figure 1:
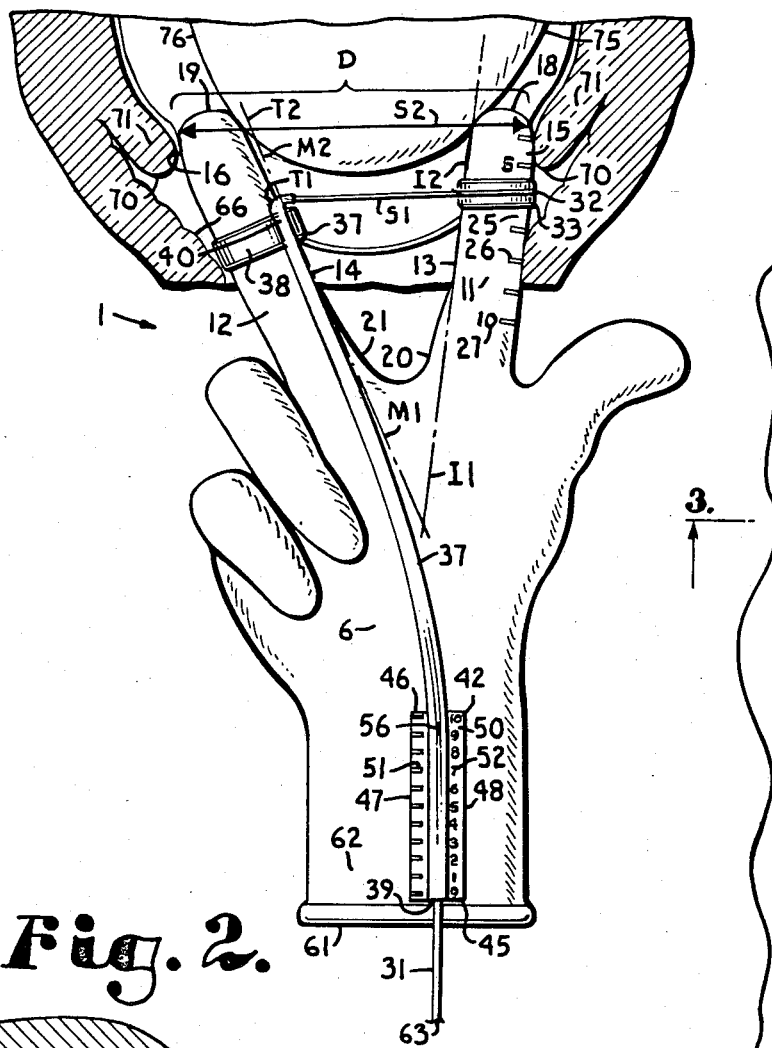
FIG. 1 is a front elevation of a glove embodying the present invention being used for determining a patient's cervical dilatation.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

DETAILED DESCRIPTION OF THE PREFERRED EMBODIMENTS

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, the reference numeral 1 generally designates an examining glove embodying the present invention. The glove 1 is preferably constructed primarily of a flexible, durable material, such as seamless rubber, which closely adheres to the examiner's hand and fingers. For example, the latex or vinyl material used for standard rubber surgical gloves is suitable. The examining glove 1 includes a back (not shown) and a front 6. Index and middle fingers 11, 12 have mutually opposed inner sides 13, 14 respectively and outwardly-facing outer sides 15, 16 respectively. The fingers 11, 12 include respective tips 18, 19 and bases 20, 21.

An index finger scale 25 extends along the index finger outer side 15 approximately from the tip 18 to the base 20 thereof and includes a plurality of markings 26 spaced at, for example, one centimeter increments. Reference numerals 27 are printed on the index finger 5 adjacent to the corresponding markings 26.

Figure 2:
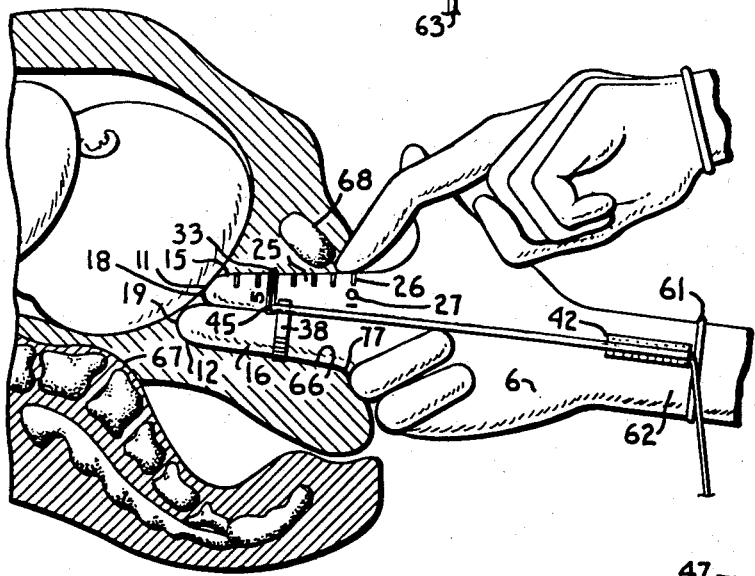
FIG. 2 is a front elevation of the glove being used to determine fetal advancement as during labor.
Figure 4:
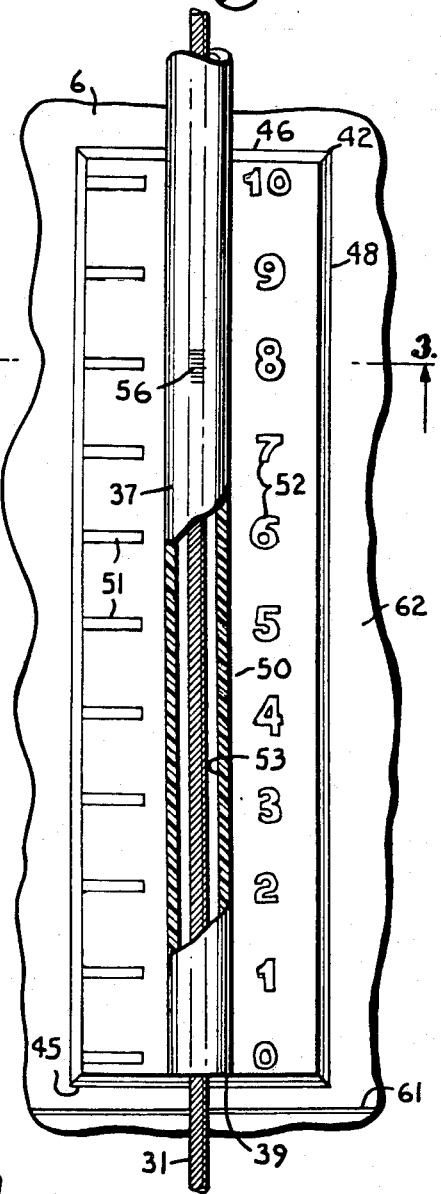
FIG. 4 is an enlarged, fragmentary front elevation of the glove particularly showing the guide tube and calibrations therefor with portions broken away to reveal internal construction.

A measuring string 31 is provided on the glove 1 as shown in FIG. 1. The measuring string 31 includes a distal end 32 embedded in an annular string attachment 33 encircling the index finger 11 positioned in spaced relation between the index finger tip 18 and base 20, preferably closer to the former. The measuring string 31 extends from the string attachment 33 at the index finger inner side 13 and is slidably received in a bore 53 of a guide tube 37. The guide tube 37 includes proximate and distal ends 39, 40, the former being attached to the middle finger by an annular, middle finger guide tube attachment 38 located between the middle fingertip and base 19, 21 so that the guide tube proximate end is located adjacent to the measuring string distal end attachment 33 when the index and middle fingers 11, 12 are placed together in juxtaposed relation, as shown in FIG. 2.

The guide tube 37 extends longitudinally along the middle finger 12 to its base 21 and along the glove front 6. The guide tube 37 is preferably transparent or translucent.

Figure 3:
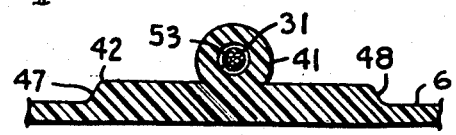
FIG. 3 is an enlarged cross-section of the glove taken generally along line 3—3 in FIG. 1 and showing a measuring string and a guide tube therefor.

The guide tube 37 is attached to the glove front 6 by a guide tube attachment panel 42 which is preferably integrally formed with the glove 1 (FIG. 3). The guide tube attachment panel 42 has a rectangular configuration with proximate and distal ends 45, 46 and opposite first and second side margins 47, 48. The guide tube 37 terminates at its proximate end 39 adjacent to the attachment panel proximate end 45, which in turn is positioned in close proximity to a cuff 61 on a wrist area 62. A plurality of marks 51 forming a string travel scale 50 are imprinted on the guide tube attachment panel 42 along the first side margin 47 thereof at regularly-spaced intervals of, for example, one centimeter each. Along the second side margin 48 of the guide tube attachment panel 42 are measuring string reference numerals 52, each positioned opposite a respective mark 51.

As shown in FIG. 3, the guide tube 37 is preferably integrally formed with the guide tube attachment panel 42 and the rest of the examining glove 1. The measuring string 31 includes a reference mark 56 which is generally located within the bore 53 and is visible through the guide tube 41. The measuring string 31 extends from the bore 53 at the attachment panel proximate end 45, past the cuff 61 and terminates at a string proximate end 63. Preferably the measuring string 31 is of sufficient length so that it is always readily accessible at the examiner's wrist, even with the fingers 11, 12 spread apart.

The guide tube 37 comprises first slip connection means for the measuring string 31 on the middle finger 12 and second slip connection means therefor on the glove front 6 adjacent to the scale 50. Therefore, it will be appreciated that the guide tube 37 need not necessarily be continuous, and could comprise two discreet guide tubes at the aforementioned locations.

In use, the index finger scale 25 is adapted for measuring the conjugate diamater of a patient prior to the onset of labor. The examiner inserts the extended index and middle fingers 11, 12 into the patient's vagina. The middle finger tip 19 is placed against the sacral promontory 67 and the index finger base 20 is placed against the lower edge of the pubis 68. The examiner then uses his or her other hand (also preferably gloved) to locate the position of the pubis 68 on the index finger scale 25. The index finger scale reference numerals 27 are intended to provide the examiner with a starting point for arriving at the patient's true conjugate diameter. For example, since the measurement is generally taken diagonally at the excessible part of the pubis, the true conjugate diameter is usually about 1.5 to 2 centimeters less than the measurable conjugate diameter. Also, the examiner may wish to adjust the observed measurements to take into account the length of his or her middle finger. However, since the latter adjustment remains constant and even the former adjustment does not vary greatly between patients, it is anticipated that the examiner will automatically subtract or add his or her constant to the observed measurement to arrive at a relatively close approximation of each patient's conjugate diameter.

The glove 1 employs the trigonometric principle that similar triangles have identical ratios between their respective, corresponding sides. As shown in FIG. 1, imaginary triangles T1 and T2 are formed when the index and middle fingers 11, 12 are spread. T1 is completely contained within T2. Triangle T1 is formed by S1 representing the spacing between the string attachment 33 at the index finger inner side 13 and the guide tube distal end 40 at the middle finger inner side 14; I1 taken along the index finger inner side 13; and M1 taken along the middle finger inner side 14 and substantially following the measuring string 31. Triangle T2 is formed by lines S2, I2 and M2, where I2 and M2 are colinear with I1 and M1 respectively. S2 is the distance between the fingertips 18, 19 at their respective inner sides 13, 14. From trigonometry, it will be apparent that since T1 and T2 are similar triangles:

$$S1/S2 = I1/I2 = M1/M2;$$

and $$S2 = (S1 \times I2)/I1 = (S1 \times M2)/M1$$

The internal dimension sought by the use of the examing glove 1 is the distance or diameter D between the fingertips 18, 19 at the finger outer sides 15, 16. As shown in FIG. 1, D is represented by S2 plus a constant K defined as the combined thickness of the fingers 11, 12 at their respective tips 18, 19. The desired dimension D is found by adding constant K to S2, for example:

$$D = ((S1 \times I2)/I1) + K = ((S1 \times M2)/M1) + K$$

From the foregoing it will be apparent that the examiner merely has to determine values for K and either I1, I2 or M1, M2 in order to compute D with the examining glove 1. These values are relatively constant for each examiner and thus need be determined only once. S1, of course, represents the distance that the measuring string 31 travels as observed on the front 6 of the examining glove 1. It is anticipated that most medical practitioners using the glove 1 will correlate the reference numerals 52 on the guide tube attachment panel 42 to actual measurements corresponding to D. This may readily be accomplished with the use of a ruler. In most cases, it is not the absolute accuracy of the measurement D that is important but rather whether the measurement D is changing during labor over the course of timed serial measurements.

FIG. 1 shows the glove 1 being used to determine a patient's cervical dilation or diameter of the internal cervical os D, representing the distance between the lower lips or rim 70 of the cervix 71. To measure the patient's cervical dilation, the examiner places the index and middle fingers 11, 12 together in juxtaposed, extended relationship. With the fingers 11, 12 placed together, all of the slack in the measuring string 31 is taken up by pulling on the measuring string proximate end 45. With the fingers 11, 12 closed, the string attachment 33 and the middle finger tube 37 are against each other. The fingers 11, 12 are then inserted into the patient's vagina 66 and the fingertips 18, 19 are placed just inside the cervix 71 with the finger outer sides 15, 16 engaging the cervical lips 70.

When the examiner spreads the fingers 11, 12 to engage the cervical lips 70, the measuring string 31 is drawn through the guide tube 37 whereby the reference mark 56 is advanced along the marks 51. The distance that the reference mark 56 advances represents S1 in the above formulae. The cervical dilation D can then be found by applying the above formulae or preferably by correlating the position of the reference mark 56 with a known value for D.

The string attachment 33 and the guide tube distal end 40 are located in spaced relation between the fingertips 18, 19 and bases 20, 21 so that in the advanced stages of labor the fetal head 76 may be located partly between the fingertips 18, 19 without interferring with the straight line S1 formed by the measuring string 31 in its extended position (FIG. 1.).

If the examiner wishes to retake the measurement D, this can be easily accomplished without removing the fingers 11, 12 from the patient's vagina 66. The examiner merely closes the fingers 11, 12 and takes up the slack in the measuring string 31 by pulling on the proximate end 63 thereof, which of course extends from the proximate end 45 of the guide tube 37. The measuring process can then be repeated as often as necessary to verify previous results. Since repeated measurements can be taken without removing the fingers 11, 12, the patient is not subjected to the risk of infection due to the glove becoming contaminated between withdrawals and insertions.

It will be appreciated that each person who uses an examining glove 1 can easily correlate the advancement of the reference mark 56 with respect to the scale 51 to the spread of the fingertips 18, 19 at the finger outer sides 15, 16. Thus, relatively accurate measurements are obtainable and consistently repeatable. Also, the results should be consistent among several examiners checking the same patient so that the progress of a patient's labor can be accurately monitored with a minimum number of examinations. In particular, the rate of change of cervical dilation can be accurately observed and predicted.

Given the patient's dilation at a particular time and the rate of change, a relatively accurate prediction of when the patient will be fully dilated or complete can be made, and the obstetrician can be summoned for the second stage of labor in ample time to make adequate preparations but without incurring undue delays which are often associated with inaccurate readings of cervical dilation. Medical practitioners can thereby schedule their time more efficiently without reducing the level of care provided to their patients.

Prior to the onset of labor, the examining glove 1 may also be used to determine the patient's bisischial diameter. The examiner inserts the extended index and middle fingers 11, 12 into the patient's vagina and places the tip of each finger against a respective ischial spine (not shown).

As an alternative to the measuring string scale 50, a plurality of marks may be placed on the measuring string 31 and, for example, a single mark can be placed in proximity to the hand tube 41.

FIG. 2 shows the glove 1 being used to monitor the progress of descent of the fetus 75. The position of the fetus 75 is commonly designated by referring to its "station", meaning the distance between the lowermost portion of the fetal head 76 and a line between the ischial spines. Negative stations represent distance in centimeters that the head is above the line between the ischial spines and positive stations represent the distance below. When the baby's head is at positive station 5, it should be visible and it is said to be "crowning".

To determine the station of the fetus 75, the examiner places the extended fingers 11, 12 together and inserts them into the vagina 66 until a middle finger tip 19 contacts the fetal head 76. The distance between the fetal head 76 and the vaginal opening 77 is then determined by using the index finger scale 25 as shown in FIG. 2. A second measurement is then taken from the vaginal opening 77 to one of the ischial spines and the difference represents the station of the fetus 75. Of course, if the latter dimension is greater than the former the station is positive and vice versa.

It is to be understood that while certain forms of the present invention have been illustrated and described herein, it is not to be limited to the specific forms or arrangement of parts described and shown. For example, the guide tube distal end 40 may be located on the index finger 11 and the string attachment 33 may be located on the middle finger 12. Also, the measuring string 31 could include a plurality of reference marks 56 for use in conjunction with a single, fixed reference mark 51 on the panel 42 adjacent to the guide tube 37.

What is claimed and desired to be secured by Letters Patent is as follows:

1. An examining glove, which comprises:
   (a) a first finger;
   (b) a second finger;
   (c) a measuring string having distal and proximate ends;
   (d) string attachment means fixedly attaching said string distal end to said first finger;
   (e) first slip connection means connecting said measuring string to said second finger;
   (f) second slip connection means connecting said measuring string to said glove in spaced relation from said fingers;
   (g) said measuring string being adapted to slip with respect to said first and second slip connection means; and
   (h) reference means associated with said measuring string and said second slip connection means adapted for determining measuring string travel associated with said measuring string slippage.

2. The examining glove according to claim 1 wherein said first and second slip connection means comprise a guide tube with a bore slidably receiving said measuring string therein.

3. The examining glove according to claim 2 wherein said guide tube includes:
   (a) a distal end mounted on a side of said second finger adjacent to said first finger.

4. The examining glove according to claim 1 wherein:
   (a) said string attachment means is positioned on a side of said first finger adjacent to said second finger.

5. The examining glove according to claim 1 wherein:
(a) said string attachment means and said first slip connection means are each located in spaced relation from tips of said first and second fingers respectively.

6. The examining glove according to claim 1 wherein:
(a) said glove includes a front; and
(b) said second slip connection means is mounted on said glove front.

7. The examining glove according to claim 1 wherein said reference means comprises:
(a) a plurality of indicia associated with said second slip connection means; and
(b) a reference mark on said string adapted to be selectively positioned adjacent to said indicia.

8. The examining glove according to claim 1, which includes:
(a) a scale along said first finger.

9. An examining glove, which comprises:
(a) a front;
(b) a back;
(c) an index finger with a tip and a base;
(d) a middle finger with a tip and a base;
(e) a measuring string having proximate and distal ends;
(f) measuring string attachment means attaching said measuring string distal end to one of said index and middle fingers;
(g) a guide tube having:
(1) a bore slidably receiving said measuring string;
(2) a distal end mounted on the other of said index and middle fingers; and
(3) a proximate end mounted on one of said front and said back of said examining glove;
(h) scale means associated with one of said measuring string and said guide tube; and
(i) reference means associated with the other of said measuring string and said guide tube, said scale means and said reference means being adapted for indicating the relative position of said measuring string with respect to said guide tube.

10. The examining glove according to claim 9 wherein:
(a) said guide tube distal end is mounted on a side of said other finger adjacent to said one finger.

11. The examining glove according to claim 10 wherein:
(a) said measuring string attachment means is positioned on a side of said one finger adjacent to said other finger.

12. The examining glove according to claim 9 wherein:
(a) said measuring string attachment means and said guide tube distal end are each located in spaced relation from said tips of said respective fingers.

13. The examining glove according to claim 9 wherein said scale means includes:
(a) a plurality of reference numerals and marks extending parallel to said hand tube.

14. The examining glove according to claim 9 wherein:
(a) said reference means includes a plurality of reference marks on said measuring string; and
(b) said scale means includes a reference mark associated with said hand tube.

15. The examining glove according to claim 9 which includes:
(a) a cuff adapted to encircle the wrist of a wearer of said glove; and
(b) said measuring string proximate end being adapted to extend beyond said cuff when said index and middle fingers are spread.

16. The examining glove according to claim 9, which includes:
(a) a scale positioned on a side of said index finger away from said middle finger.

17. An examining glove, which comprises:
(a) a front;
(b) a back;
(c) an index finger with a tip and a base;
(d) a middle finger with a tip and a base;
(e) said fingers having adjacent inner sides and outer sides positioned away from each other;
(f) a measuring string having distal and proximate ends;
(g) a measuring string attachment comprising a band encircling one of said index and middle fingers in spaced relation between its tip and its base, said measuring string distal end being attached to said attachment band at the inner side of said one finger;
(h) a guide tube having:
(1) a bore slidably receiving said measuring string;
(2) a distal end mounted on the other of said index and middle fingers; and
(3) a proximate end mounted on one of said front and said back of said examining glove;
(i) a scale associated with said guide tube; and
(j) said measuring string having a mark movable along said scale in proportion to a distance between said measuring string attachment and said finger tube.

18. The examining glove according to claim 17 wherein:
(a) said measuring string attachment band is integrally formed with said one finger and thicker than the remainder thereof.

19. The examining glove according to claim 17, which includes:
(a) a guide tube distal end attachment comprising an annular band integrally formed with said other finger and thicker than the remainder thereof.

20. The examining glove according to claim 17, which includes:
(a) a guide tube attachment panel integrally formed with the front of said glove and said guide tube, said panel being thicker than the remainder of said examining glove front; and
(b) said scale comprising a plurality of marks on said hand tube attachment panel extending along one side of said guide tube and a plurality of reference numerals on said attachment panel and extending along the other side of said guide tube.

* * * * *